(12) United States Patent
Best

(10) Patent No.: US 8,887,371 B1
(45) Date of Patent: *Nov. 18, 2014

(54) FITTING TO SECURE TUBING WITHIN A CPI PORT P08-1020

(76) Inventor: John W. Best, State College, PA (US)

( * ) Notice: Subject to any disclaimer, the term of this patent is extended or adjusted under 35 U.S.C. 154(b) by 276 days.

This patent is subject to a terminal disclaimer.

(21) Appl. No.: 13/191,756

(22) Filed: Jul. 27, 2011

Related U.S. Application Data

(63) Continuation-in-part of application No. 12/255,952, filed on Oct. 22, 2008, now Pat. No. 8,006,367.

(60) Provisional application No. 61/000,149, filed on Oct. 24, 2007.

(51) Int. Cl.
 *B21D 39/00* (2006.01)
(52) U.S. Cl.
 USPC .............................. 29/520; 29/516; 29/890.15

(58) Field of Classification Search
 USPC .............. 29/520, 516, 890.15, 451, 515, 237; 285/339, 341, 342, 343, 354
 See application file for complete search history.

(56) References Cited

U.S. PATENT DOCUMENTS

| 6,494,500 | B1 * | 12/2002 | Todosiev et al. | ............... | 285/342 |
| 7,681,926 | B2 * | 3/2010 | Valaskovic et al. | ........... | 285/342 |
| 7,784,838 | B2 * | 8/2010 | Levy | .............................. | 285/342 |
| 8,006,367 | B1 * | 8/2011 | Best | ............................... | 29/520 |

* cited by examiner

*Primary Examiner* — David E Bochna
(74) *Attorney, Agent, or Firm* — John J. Elnitski, Jr.

(57) ABSTRACT

A fitting and method of use that includes a tubing channel to receive tubing. The fitting includes a fitting body having the tubing channel to receive the tubing and having exterior threading to engage internal threading of a CPI type port. The fitting includes a first ferrule that receives the tubing. The fitting has a cap with a closed end and an open end. The cap has internal threading to engage the exterior threading of the fitting body and a hole to receive said tubing. The fitting has a second ferrule that receives the tubing.

2 Claims, 10 Drawing Sheets

FITTING TO SECURE TUBING WITHIN A CPI PORT P08-1020

This application claims the benefit of and incorporates by reference U.S. Provisional Application No. 61/000,149 filed Oct. 24, 2007, U.S. patent application Ser. No. 12/255,952 filed Feb. 22, 2008 and U.S. Pat. No. 8,006,367. This application is a Continuation In Part of U.S. patent application Ser. No. 12/255,952 filed Feb. 22, 2008.

BACKGROUND

The present invention generally relates to the field of liquid chromatography. More specifically, the present invention relates to fittings used as coupling devices that couple narrow diameter tubing and Chemical Process Industry (CPI) ports of an apparatus together.

It is desirable to make connections of small diameter tubing to a receptacle of an apparatus in such a way as to allow high pressure levels of liquid to be attained in the tubing without fluid leakage at the connections. It is additionally desirable to make a union between the tubing and an apparatus in such a way as to maintain a fluid stream of a consistent diameter as the fluid is pumped under pressure to or from the apparatus through the tubing.

To those skilled in the art, a preferred method of making the connection between tubing and a fluid handling or analysis apparatus is to use a Chemical Process Industry (CPI) port, or 10-32 CPI port, or HPLC port as part of the apparatus. These terms refer to a port having a cavity that includes a threaded section, a conical section which reduces in the diameter and receives a compression ferrule, and a bottom cylindrical section. The bottom cylindrical section has a diameter that allows a snug fit of the tubing. The bottom cylindrical section has a flat bottom, against which is intended to form a void free interface between tubing and the CPI port. Together, the threaded section, conical section, bottom cylindrical section and flat bottom of the bottom cylindrical section comprise a receptacle or port into which is inserted a tube. The tube passes through a conical coupling device or ferrule that is inserted into the CPI port with the tube. The conical coupling device or ferrule is compressed against the tube as the coupling device enters the conical section of the CPI port, thereby clamping and sealing the tubing in the CPI port.

Present coupling devices for coupling tubing to the CPI port are limited with regard to the maximum operating pressure which can be attained with their use. The coupling devices are additionally limited with regard to positive means to eliminate a parasitic effect known to those skilled in the art as 'dead volume' of a connection. Dead volume refers to any deviation from a cylindrical fluid path through the tubing and connection into the CPI port. This effect occurs when the distal end of the tubing is not secured completely into the CPI port with maximum insertion of the tubing against the flat bottom of the bottom cylindrical section. The effect of dead volume can also be present when tubing is deformed due to over tightening of compression fittings, or improper cutting of tubing ends.

Present coupling devices consist of a threaded member which screws to the CPI port and drives a cone shaped ferrule about the tubing into the CPI port to provide clamping and sealing forces on the tubing. One present coupling device is a one-piece molded combination coupling device which combines the threaded member and the cone shaped ferrule into a single unit. The combination coupling device is convenient, but has undesirable limitations in maximum holding pressure. The combination coupling device can also create a parasitic volume at the interface between tubing and the CPI port, thus causing an undesirable dilution of chemicals being transported in solution through the tubing. Another coupling device is referred to as a 'two piece fitting'. The two piece fitting is comprised of a cone shaped ferrule, which is compressed by a separate threaded section, to form a seal about the tubing. The two piece fitting has an advantage over the combination device because it can withstand slightly higher pressures, but is not adequately foolproof in it's ability to avoid creation of parasitic dead volumes. Yet another coupling device applies a force by means of an internal spring against the cone shaped ferrule along the axis of fluid transport within the tubing. The axial force is continuously applied as the coupling device is tightened to provide clamping and sealing force to the cone shaped ferrule, thereby reducing the possibility of a parasitic dead volume being created. This approach represents the state of the present art with respect to elimination of parasitic dead volume, and ease of use.

All three aforementioned approaches are limited by the ability of a single cone shaped ferrule to hold the tubing by means of friction applied by virtue of the compression of the cone shaped ferrule within the CPI port. Furthermore, in the case of the spring assisted coupler, if a connection is attempted while fluid is being pumped to or from the tubing, fluid pressure will build as the ferrule is being compressed. This causes the tubing to slide back against the spring force along the axis of fluid flow, causing a parasitic volume to be formed at the junction between the interface of the tubing and the CPI port. Also, in each of the previous approaches, even when the fitting is properly installed and using carefully prepared tubing, there is a negative artifact of the design of the CPI port itself. The negative artifact of the design allows radial migration of fluids at the interface between the tip of the tubing and the flat bottom of the CPI port.

Another aspect of present day coupling devices is the practice of using tubing of a smaller diameter than the bottom cylindrical section of the CPI port. The bottom cylindrical section is located at the bottom of the CPI port and is usually one sixteenth of an inch in diameter. Tubing of one thirty-second inch diameter are commonly used with special ferrules in which a cylindrical section and a cone shaped section are combined end-to-end in a unified compression fitting and diameter adaptor. The cylindrical section forms a sleeve, which adapts the diameter of the inner tubing to the diameter of the CPI port. A shortcoming of this approach is that the cone shaped section compresses, while the cylindrical shaped adaptor does not. This causes a void volume about the perimeter of the tubing and the perimeter of the cylindrical shaped section of the ferrule-adaptor. Furthermore, this type of ferrule-adaptor is supplied with a fixed length cylindrical section, hence it is unable to adapt to CPI ports with deeper than average bottom cylindrical section.

A final aspect of present day coupling devices lies in coupling device failure. When pressures of fluids which are being transported through the port increase, a component of the pressure exerts a longitudinal force along the axis of the tubing being clamped by the compression ferrule. This longitudinal force is countered solely by frictional force between the inside of the ferrule and the tubing where the ferrule contacts the tubing. As fluids within the tubing and volumes are pressurized and de-pressurized, a phenomenon known as 'creep' can occur. Creep causes an ever increasing void to form between the tip of the tubing and the surface of the flat bottom of the CPI port. Eventually, the tip of the tubing will be pushed back towards and through the ferrule, causing it to leak severely, incapacitating the analytical system, and possibly creating a safety hazard. To those skilled in the art, this failure is known as a 'tubing blow-out'.

What is needed is a coupling device which can relieve the longitudinal forces between the tubing and ferrule, and allow greater longitudinal force to be applied to the tubing during and immediately after the application of radial compressive forces to the ferrule. Furthermore, it is desirable to have the ability to positively remove parasitic volumes created by either compression of the cone shaped ferrule, or variation in CPI port geometry, especially depth. Furthermore, it is desirable to have the ability to adapt narrow gauge tubing of 1/32" and lower to be connected to CPI ports manufactured for 1/16" tubing, without the use of a separate sleeve type adaptor. And furthermore the ability to capture or retain the tubing in the event of failure of the primary ferrule is desirable. Wherein, retaining the tubing should be accomplished in such a way as to eliminate creeping effect of dead volume, and further to eliminate 'tubing blow out' failure. Ideally, the aforesaid features would be implemented by a design which could be tightened by a single method of activation to couple the tubing to the CPI port. Further, it is desirable that the coupling device be compact as to allow insertion in areas congested with various components of an HPLC or UHPLC apparatus. Also, it is desirable to apply adequate longitudinal force to the tip of the tubing, thus allowing for a new type of primary seal to be achieved at the tip of the tubing and achieving a connection for communication of fluids with the lowest practical parasitic volume. That is to say, it is desirable to achieve a diskular seal at the bottom of the port, rather than a conical seal at the compressed ferrule.

It is an object of the present invention to provide a device that allows coupling between narrow tubing and a fluid handling device using a CPI port in such a way as to eliminate fluid leakage when fluid is pressurized.

It is an object of the present invention to provide a device that employs a positive method to eliminate dead volume at the interface between tubing and an interior of a CPI port.

It is an object of the present invention to provide a device to apply additional forces within an area of interface between tubing and a CPI port in such a way as to improve the ability to resist tubing creep.

SUMMARY OF THE INVENTION

A fitting and method of use that includes a tubing channel to receive tubing. The fitting includes a fitting body having the tubing channel to receive the tubing and having exterior threading to engage internal threading of a CPI type port. The fitting includes a first ferrule that receives the tubing. The fitting has a cap with a closed end and an open end. The cap has internal threading to engage the exterior threading of the fitting body and a hole to receive said tubing. The fitting has a second ferrule that receives the tubing.

DETAILED DESCRIPTION

The present invention is an improved fitting for securing tubing into a receptacle of an apparatus, through which fluids may be passed at high pressures without leakage. The fitting is installed upon tubing to be connected to the apparatus. The fitting allows for the reduction of dead volume associated with the union of the tubing with the receptacle. The fitting is considered miniaturized in relation to the pressure carrying capacity, so that the fitting can be used in confined spaces. The fitting is designed for use in new generation ultra high performance liquid chromatography, referred to as UPLC or UHPLC. UPLC or UHPLC devices have demonstrated handling pressures of greater than fifteen thousand pounds per square inch. The fitting may be used on one end of a length of tubing or on both ends of a length of tubing.

Figure 1:
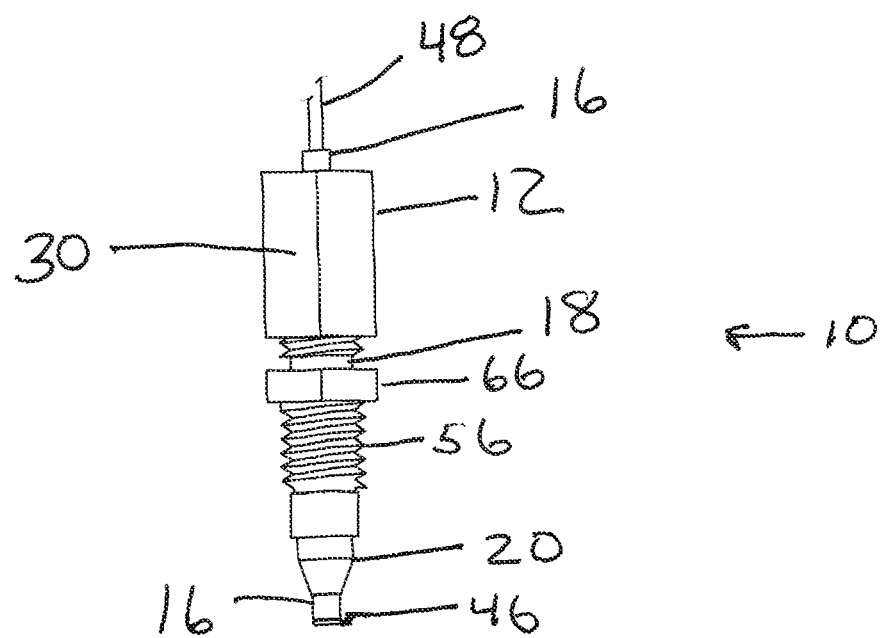
FIG. 1 is a side view of a fitting according to the present invention.
Figure 2:
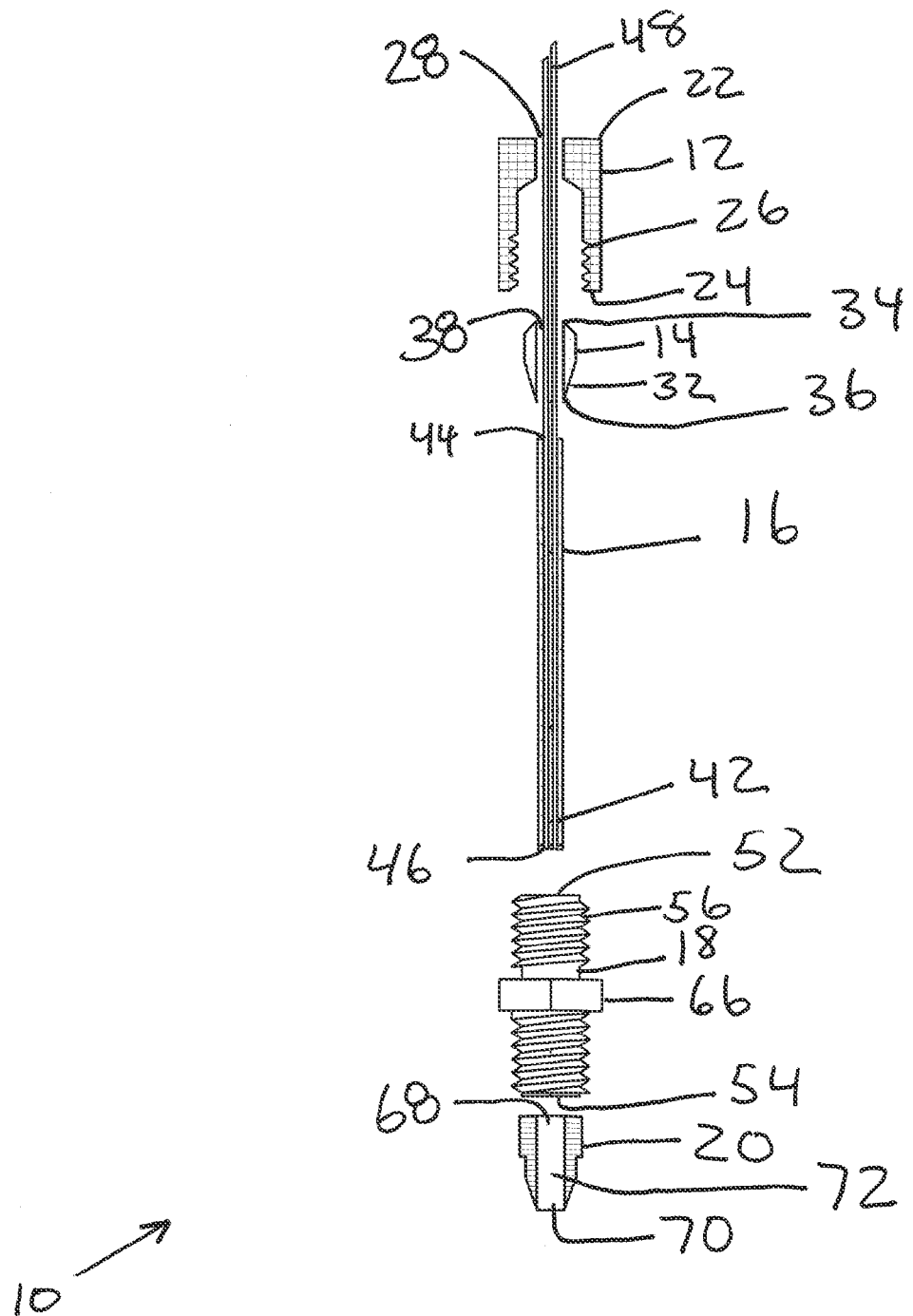
FIG. 2 is an exploded side cutaway view of a fitting according to the present invention.

FIG. 1 shows an assembly view and FIG. 2 shows an exploded view of the parts of a fitting 10 according to the present invention. The fitting 10 includes a cap 12, first ferrule 14, terminator pin 16, fitting body 18 and second ferrule 20. The cap 12 includes a closed end 22 and an open end 24. The cap 12 includes internal threading 26 which is accessible from the open end 24. The closed end 22 includes a tube hole 28 sized to receive the terminator pin 16. A preferred material used for the cap 12 is anodized aluminum or stainless steel. The cap 12 is shown having an outside surface 30 in a hex shape to allow the use of a wrench to turn the cap 12. The cap 12 may also have a knurled outside surface to facilitate gripping by the user's fingers, so that the user can easily turn the cap 12 without the use of a tool. A first embodiment of the first ferrule 14 includes a short compressible conical section 32. The first embodiment of the first ferrule 14 includes an open entrance end 34, open exit end 36 and a through hole 38 between the entrance end 34 and exit end 36. The first embodiment uses polymeric material such as Poly Ether Ether Ketone which is capable of sliding along the outside surface of the terminator pin 16 to be inserted into the first ferrule 14, even after the fitting 10 has been used and reused by repeated install and removal of the fitting 10. A second embodiment of the first ferrule 14 is to use what is known to those skilled in the art as a 'biting' ferrule. A biting ferrule is typically metallic and has an open entrance end and an open exit end with a through hole between the entrance end and exit end. The exit end is usually smaller and is formed in such a way as to permanently and securely grip what is inserted into the first ferrule 14, without the intention of ever removing the first ferrule 14. Alternately, the biting ferrule might be a ferrule of a uniform cylinder shape which is welded, glued or crimped in place on the object inserted into the through hole of the ferrule.

Figure 3:
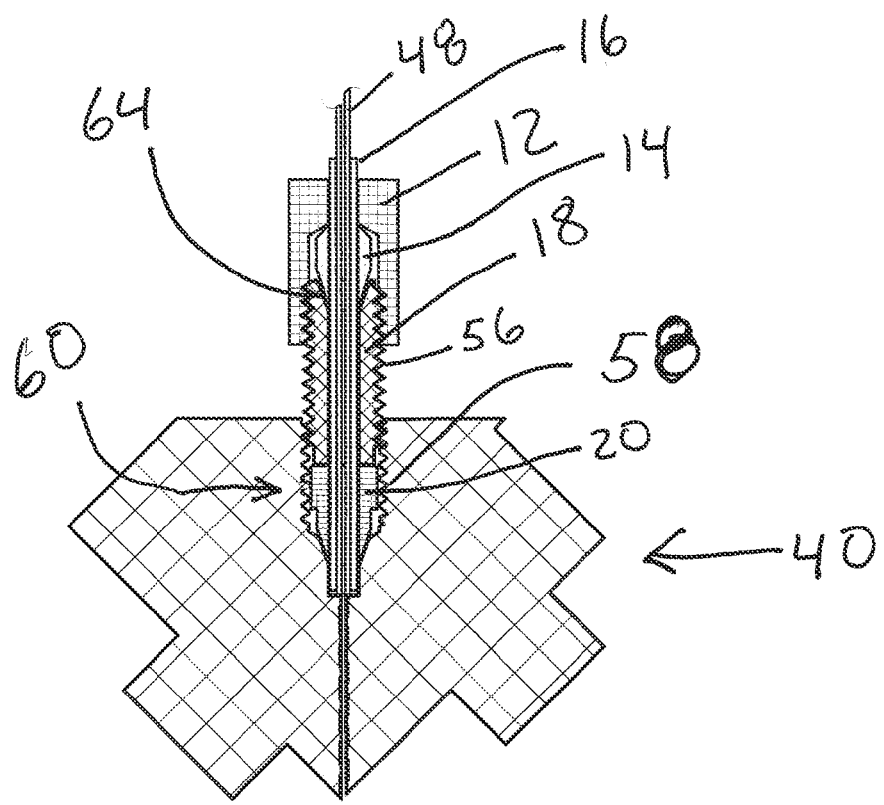
FIG. 3 is cutaway view of an exit end of a terminator pin according to the present invention.
Figure 4:
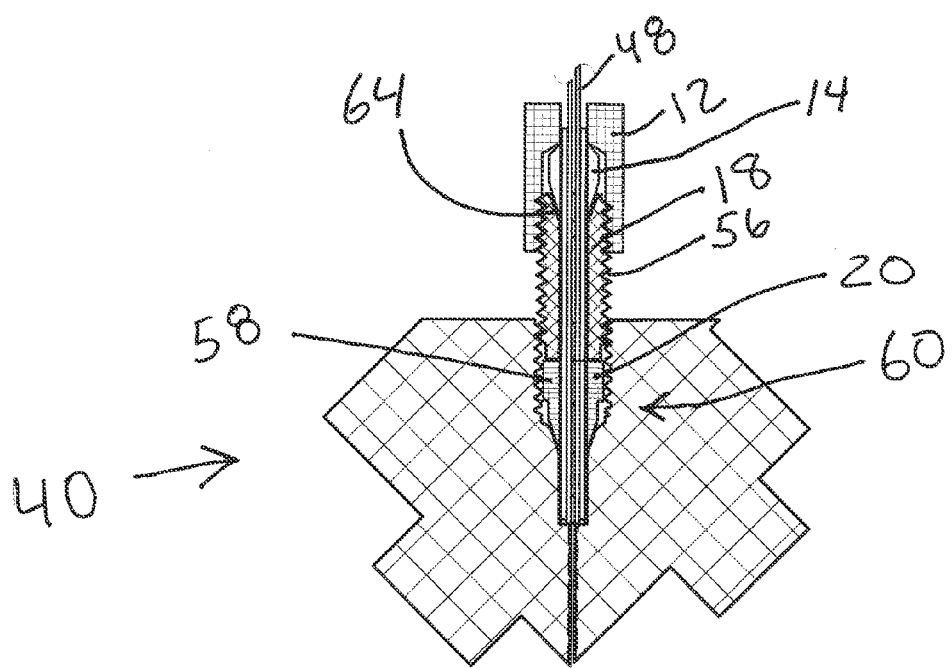
FIG. 4 is an exploded side cutaway view of a fitting according to the present invention.

The terminator pin 16 is a hollow cylinder having outside diameter of approximately one sixteenth of an inch so as to fit snugly inside the bottom cylindrical section of the CPI port 40, which usually has a diameter slightly larger than one sixteenth of an inch. The terminator pin 16 has a tubing channel 42 that is open at an entrance end 44 and an exit end 46 of the terminator pin 16. The tubing channel 42 has a diameter sized to accept smaller diameter tubing 48. Stainless steel is the preferred material for the terminator pin 16. The fitting body 18 includes a terminator pin channel 50. The fitting body 18 has a open entrance end 52 and a open exit end 54. The terminator pin channel 50 is open at both the entrance end 52 and the open exit end 54 of the fitting body 18 to allow passage of the terminator pin 16. The fitting body 18 has exterior threading 56 to allow the fitting body 18 to engage the internal threading 58 of the threaded section 60 within the CPI port 40 and allow the cap 12 to thread onto the fitting body 18, as shown in FIGS. 3-4. The fitting body 18 has a conical section 64 at the entrance end 52 of the fitting body 18 that has a geometry to receive the first ferrule 14 and allow the first ferrule 14 to be compress against terminator pin 16. The fitting body 18 can have an optional hex nut 66 as shown in FIGS. 1-2 to be a stationary part of the fitting body 18 and allow the use of a wrench to aid in removal from the CPI port 40. The second ferrule 20 is a single or multi-piece cone shaped compression fitting. The second ferrule 20 includes an open entrance end 68, open exit end 70 and a through hole 72 between the entrance end 68 and exit end 70. The second ferrule 20 is constructed of compressible material which is capable of compressing radially about the terminator pin 16 after the terminator pin 16 has been inserted into the through hole 72 of the second ferrule 20.

Figure 5:
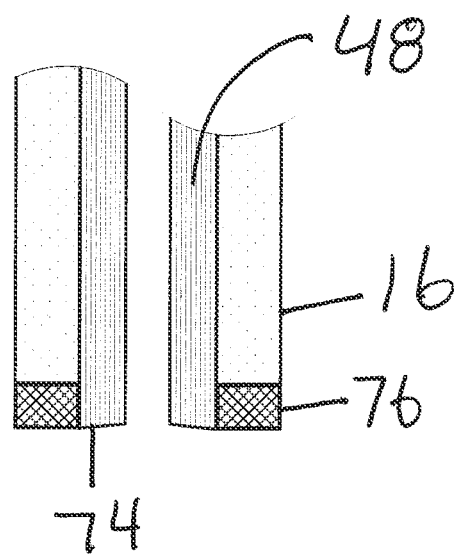
FIG. 5 is a cutaway view of a fitting according to the present invention.

Prior to connection of the fitting 10 to an apparatus, the fitting 10 is assembled. The tubing 48 shown in FIGS. 1-6 is usually composed of stainless steel. The tubing 48 will be described as having an outside diameter of approximately one thirty-second of an inch, but this merely represents any tubing having a smaller diameter than that of the bottom cylindrical section of the CPI port 40. The tubing 48 and terminator pin 16 are joined by first inserting the tubing 48 into the tubing channel 42 of the terminator pin 16 at the entrance end 44 of the terminator pin 16. The tubing 48 is inserted until the tip 74 of the tubing 48 is flush with the exit end 46 of the terminator pin 16. The tip 74 of the tubing 48 and the terminator pin 16 are secured together by welding or brazing the tip 74 of the tubing 48 to the exit end 46 of the terminator pin 16. The combination of the tip 74 of the tubing 48 and the exit end 46 of the terminator pin 16 together act as like the tip of a larger tubing that is usually used in the bottom cylindrical section of the CPI port 40. The weld or brazing also acts as a seal 76 between the tubing 48 and the terminator pin 16 at the exit end 46 of the terminator pin 16. A chamfer or bevel may be incorporated into the juncture of the tip 74 of the tubing 48 and the exit end 46 of the terminator pin 16 to facilitate an optional metal-to-metal sealing mechanism, as shown in FIG. 5. Optionally, tubing 48 can be composed of a polymer, such as Poly Ether Ether Ketone and in secured at the exit end 46 of the terminator pin 16 using an epoxy or other bonding material, in place of welding or brazing. Assembly of the fitting 10 continues by passing terminator pin 16, exit end 46 first, through the cap 12 and then through the first ferrule 14. The terminator pin 16 is then inserted through the terminator pin channel 50 of the fitting body 18 and the cap 12 is slightly screwed onto the threading 56 of the fitting body 18. Finally, the terminator pin 16 inserted through the second ferrule 20. The fitting 10 is now fully assembled and ready for use.

Figure 6:
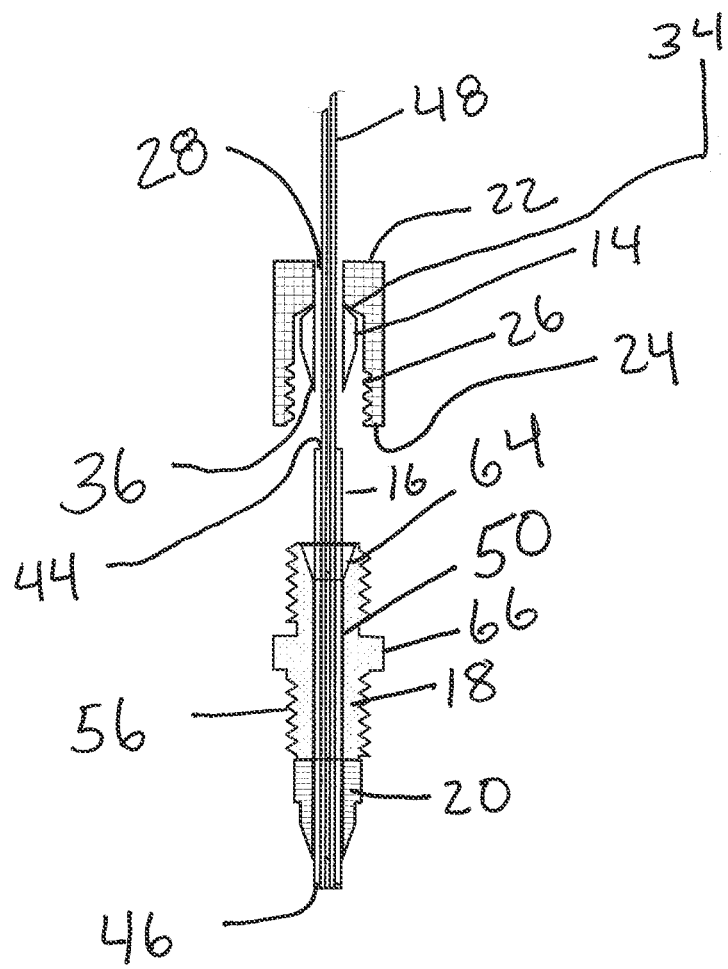
FIG. 6 is a cutaway view of a fitting according to the present invention.

The fitting 10 and tubing 48 are installed to a CPI port 40 in the following manner. Preparation of installing the fitting 10 and tubing 48 includes unscrewing the cap 12 from the fitting body 18 and pushing the terminator pin 16 with the tubing 48 attached through the first ferrule 14, fitting body 16 and second ferrule 20 so that the exit end 46 of the terminator pin 16 extends approximately 5 mm beyond the exit end 70 of the second ferrule 20, as shown in FIG. 6. The bottom cylindrical section of the CPI port 60 is intended to receive tubing 48, but instead will receive terminator pin 16 when using the fitting 10. Abnormally deep bottom cylindrical sections will require the exit end 46 of the terminator pin 16 to be extended farther from the exit end 70 of the second ferrule 20 as shown in the comparison of FIGS. 3 and 4. The first ferrule 14, fitting body 18 and second ferrule 20 are to be in close proximity to each other along the terminator pin 16. The cap 12 is replaced on the fitting body 18 without turning the cap 12 too far as to begin to compress first ferrule 14 about the terminator pin 16. The fitting 10 is then installed into the receiving CPI port 40 by grasping the cap 12 and guiding the exit end 46 of the terminator pin 12 into the CPI port 40 and pushing the fitting 10 in as far as possible, while turning the cap 12 until tight. The fitting 10 is now installed, but the mechanics of operation of the components will be reviewed for additional clarity as to the operation and attainment of the objects of the invention.

Returning to the moment when the cap 12 is first turned, it should be noted that initially the fitting body 18 begins to turn with the cap 12 and the fitting body 18 threads into the threaded section 60 of the CPI port 40. The turning action of the fitting body 18 into the threaded section 60 of the CPI port 40 pushes the second ferrule 20 into the CPI port 40. The fitting body 18 stops turning as slight pressure begins to accumulate between the second ferrule 20 and the terminator pin 16, due to compression of the second ferrule 20 as the second ferrule 20 enters the conical section of the CPI port 40.

During turning of the cap 12, the cap 12 begins to push against first ferrule 14 before the fitting body 18 begins to apply significant pressure against the second ferrule 20. As the cap 12 is turned, the cap 12 forces the first ferrule 14 into the conical section 64 at the entrance end 52 of the fitting body 18. The first ferrule 14 in turn grips the terminator pin 16 and drives the terminator pin 16 to the flat bottom of the CPI port 40, as the cap 12 continues to be turned. As the combination of forces resulting from first ferrule 14 tightening about the terminator pin 16 at the conical section 64 of the fitting body 18 begins to increase, the cap 12 begins to resist turning against the fitting body 18, causing the turning forces applied to the cap 12 to be transmitted through the first ferrule 14 and onto fitting body 18, thereby causing the fitting body 18 to again screw into the CPI port 40. As the fitting body 18 is screwed into the CPI port 40, the second ferrule 20 is driven in to the conical section of the CPI port 40, causing the second ferule 20 to be additionally compressed between the CPI port 40 and terminator pin 16 and providing a seal between the terminator pin 16 and the CPI port 40. As the second ferrule 20 begins to compress in the conical section of the CPI port 40, the second ferrule 20 offers resistance to the screwing of the fitting body 18 into the CPI port 40. As the friction between the second ferrule 20 and the terminator pin 16 increases due to tightening, there is greater resistance to insertion of fitting body 18 into the CPI port 40. This increased resistance causes the cap 12 to again turn relative to the fitting body 18. Even though only the cap 12 is actually being tighten by the user, there is a back and forth tightening progressing between the cap 12 tightening to the fitting body 18 and the fitting body 18 tightening in the CPI port 40. This back and forth tightening is caused by the back and forth compression of the first ferrule 14 and second ferrule 20, which ultimately results in the first ferrule 14 and second ferrule 20 achieving a proportional and approximately equal compression about the terminator pin 16. The total back and forth tightening and compression process happens so quickly and frequently that it is almost imperceptible. The best results will be achieved is the first ferrule 14 and the second ferrule 20 are made from a similar material and have a similar shape and size.

Once installed in the aforesaid manner, the manner of operation of the fitting 10 becomes apparent. The compression of first ferrule 14, causes friction against the terminator pin 16 relative to fitting body 18 that is securely attached in the CPI port 40. A fraction of longitudinal pressure which occurs at exit end 46 of the terminator pin 16 during normal operation of the CPI port 40 is transmitted through terminator pin 16 to first ferrule 14. This fraction of longitudinal pressure is then transmitted to the cap 12 and on to the threaded portion of fitting body 18, where the threads inside the cap 12 engage against fitting body 18. Then, the fraction of longitudinal pressure is transmitted through the fitting body 18 and back to the CPI port 40. The aforementioned fraction of longitudinal compressive pressure is a percentage of the total pressure in and around the exit end 46 of the terminator pin 16. This fraction of the total pressure force does not get retained and transmitted back to fitting body 18 of the fitting 10 through the second ferrule 20, as compared to current coupling devices. This effect amounts to the 'sharing' of forces applied to the terminator pin 16 between the first ferrule 14 and the second ferrule 20, giving the fitting substantially greater holding power of the tubing 48 against pressures applied at the exit end 46 of the terminator pin 16.

Alternately, an embodiment of the invention allows the primary method of sealing to be passed from the second ferrule 20 to the exit end 46 of the terminator pin 16. This method of sealing will be referred to as 'tip sealing', and is an entirely new method to those practiced in the state of the art. Tip sealing is accomplished by installing the fitting 10 as described above, but instead of using a sliding polymeric ferrule for the first ferrule 14, a 'biting' ferrule, or a permanently applied ferrule is employed on the terminator pin 16. In the tip sealing embodiment, turning the cap 12 causes the first ferrule 14 of the biting ferrule type to secure the first ferrule 14 against the terminator pin 16, causing a greater proportion of force to be transmitted through the terminator pin 16 to the exit end 46 of the terminator pin 16, as compared to a polymeric ferrule. In the previous embodiment, the fitting body 18 begins turning when a similar compressive equilibrium between the first ferrule 14 and the second ferrule 20 is achieved. In the tip sealing embodiment, the fitting body 18 begins to turn when the cap 12 has compressed the biting ferrule into the conical section 64 of the fitting body 18. The compression of the biting ferrule transmits the rotational force of the cap 12 to the fitting body 18. This rotational force is then transmitted to the threading of the CPI port 40, which drives the exit end 46 of the terminator pin 16 against the flat bottom of the CPI port 40. In the tip sealing embodiment, the secondary ferule 20 acts as a guide to keep the terminator pin 16 centered in the CPI port 40, but does not compress the second ferrule 20 about the terminator pin 16, so that it does not impede the exit end 46 of the terminator pin 16 from becoming compressed at the flat bottom of the CPI port and sealing at the flat bottom of the CPI port. This is due to the holding mechanism of the biting ferrule which is caused by shear forces between said biting ferrule and terminator pin 16. Most biting ferrules include an edge that digs in or bites when smaller section of the biting ferrule is compressed. This edge aides in creating the shear forces. Whereas, a 'non-biting' ferrule relies on lesser frictional forces within the ferrule's inner circumference and where these frictional forces have less holding power against slippage of terminator pin 16. The tip sealing embodiment is significant because it dramatically reduces the potential for chemical residuals to become entrapped in miniscule dead volumes which are associated with the perimeter of the cylindrical volume below the second ferrule 20 that interact with CPI port 40. In the tip sealing embodiment, the second ferrule 20 is not required to provide sealing surfaces, rather the second ferrule 20 provides mechanical stabilization of the terminator pin 16 such as to hold the terminator pin 16 concentric with the center of the open area within the CPI port 40. Another advantage of metal-to-metal sealing between the biting ferrule and the terminator pin 16 is the potential of the fitting 10 to withstand pressures in excess of the limitations of the combination of current ferrules.

A malleable metal or polymer may be applied to the exit end 46 of terminator pin 16, to allow a seal to be created between the exit end 46 of the terminator pin 16 and the flat bottom of bottom cylindrical section of the CPI port 40. The preferred material being gold, but allowing for the possibility that other materials may be employed within the spirit of the present invention. Also, the cap 12, first ferrule 14, fitting body 18 and second ferrule 20 can be used with tubing 48 that is sized to fit the bottom cylindrical section of the CPI port 40 in place of the terminator pin 16. An alternate implementation would include a terminator pin 16 of a malleable plastic that is not secured to the tubing 48. This allows the terminator pin to compress and seal against the flat bottom of the bottom cylindrical section of the CPI port 40. The two ferrules 14, 20 compress the plastic terminator pin 16 around the tubing to provide a seal between the terminator pin 16 and tubing 48.

Figure 7:
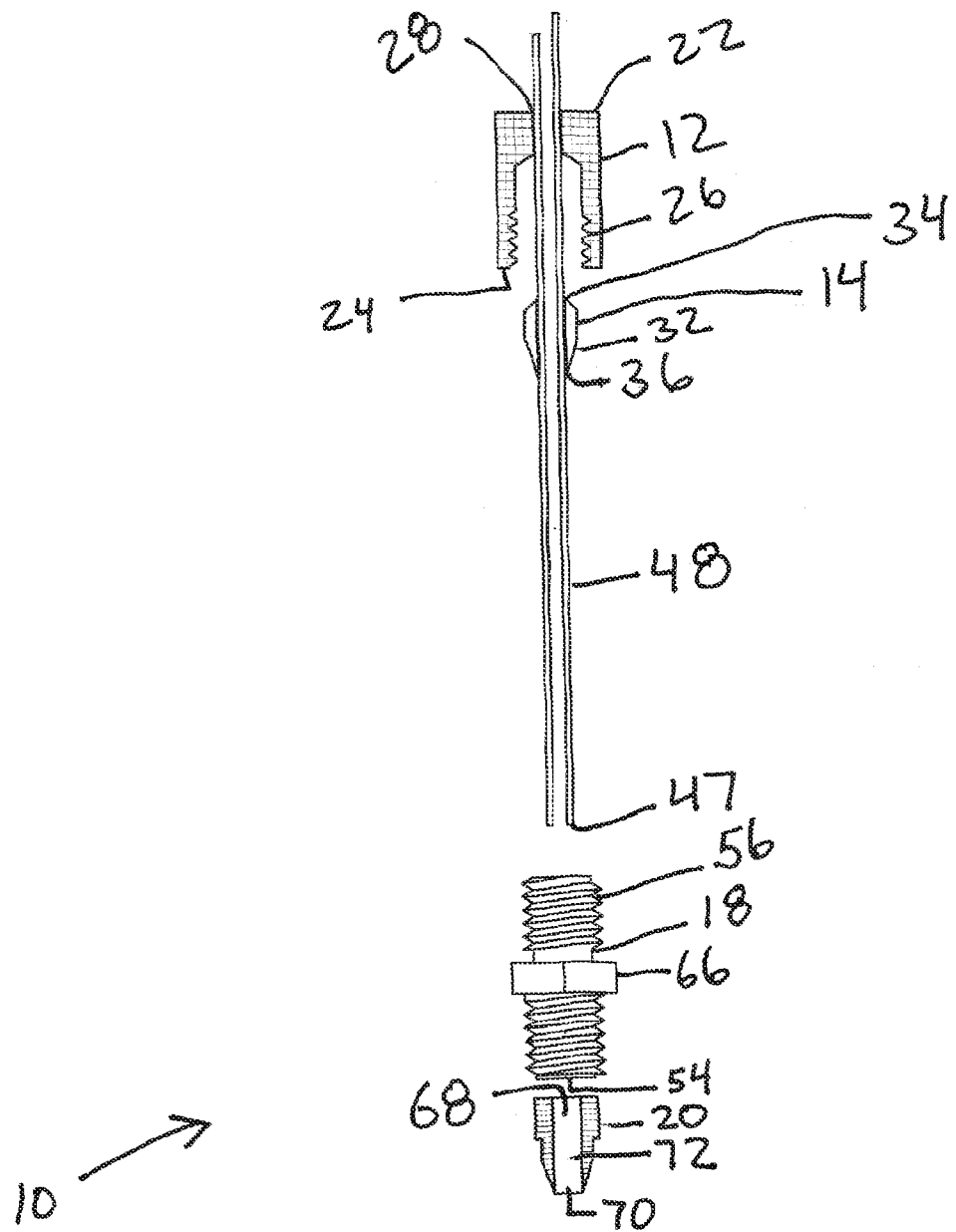
FIG. 7 is an exploded side cutaway view of a fitting according to the present invention.

FIGS. 7-10 show another embodiment of the present invention using the tubing 48 without the use of the terminator pin 16. FIG. 7 shows an exploded view of the parts of a fitting 10 according to this additional embodiment of the present invention. The fitting 10 includes a cap 12, first ferrule 14, fitting body 18 and second ferrule 20 and tubing 48. The cap 12 includes a closed end 22 and an open end 24. The cap 12 includes internal threading 26 which is accessible from the open end 24. The closed end 22 includes a tube hole 28 sized to receive the tubing 48. A preferred material used for the cap 12 is anodized aluminum or stainless steel. The cap 12 is shown having an outside surface 30 in a hex shape to allow the use of a wrench to turn the cap 12. The cap 12 may also have a knurled outside surface to facilitate gripping by the user's fingers, so that the user can easily turn the cap 12 without the use of a tool. A first example of the first ferrule 14 includes a short compressible conical section 32. The first embodiment of the first ferrule 14 includes an open entrance end 34, open exit end 36 and a through hole 38 between the entrance end 34 and exit end 36. The first embodiment uses polymeric material such as Poly Ether Ether Ketone which is capable of sliding along the outside surface of the tubing 48 to be inserted into the first ferrule 14, even after the fitting 10 has been used and reused by repeated install and removal of the fitting 10. A second example of the first ferrule 14 is to use what is known to those skilled in the art as a 'biting' ferrule. A biting ferrule is typically metallic and has an open entrance end and an open exit end with a through hole between the entrance end and exit end. The exit end is usually smaller and is formed in such a way as to permanently and securely grip what is inserted into the first ferrule 14, without the intention of ever removing the first ferrule 14. Alternately, the biting ferrule might be a ferrule of a uniform cylinder shape which is welded, glued or crimped in place on the object inserted into the through hole of the ferrule.

Figure 8:
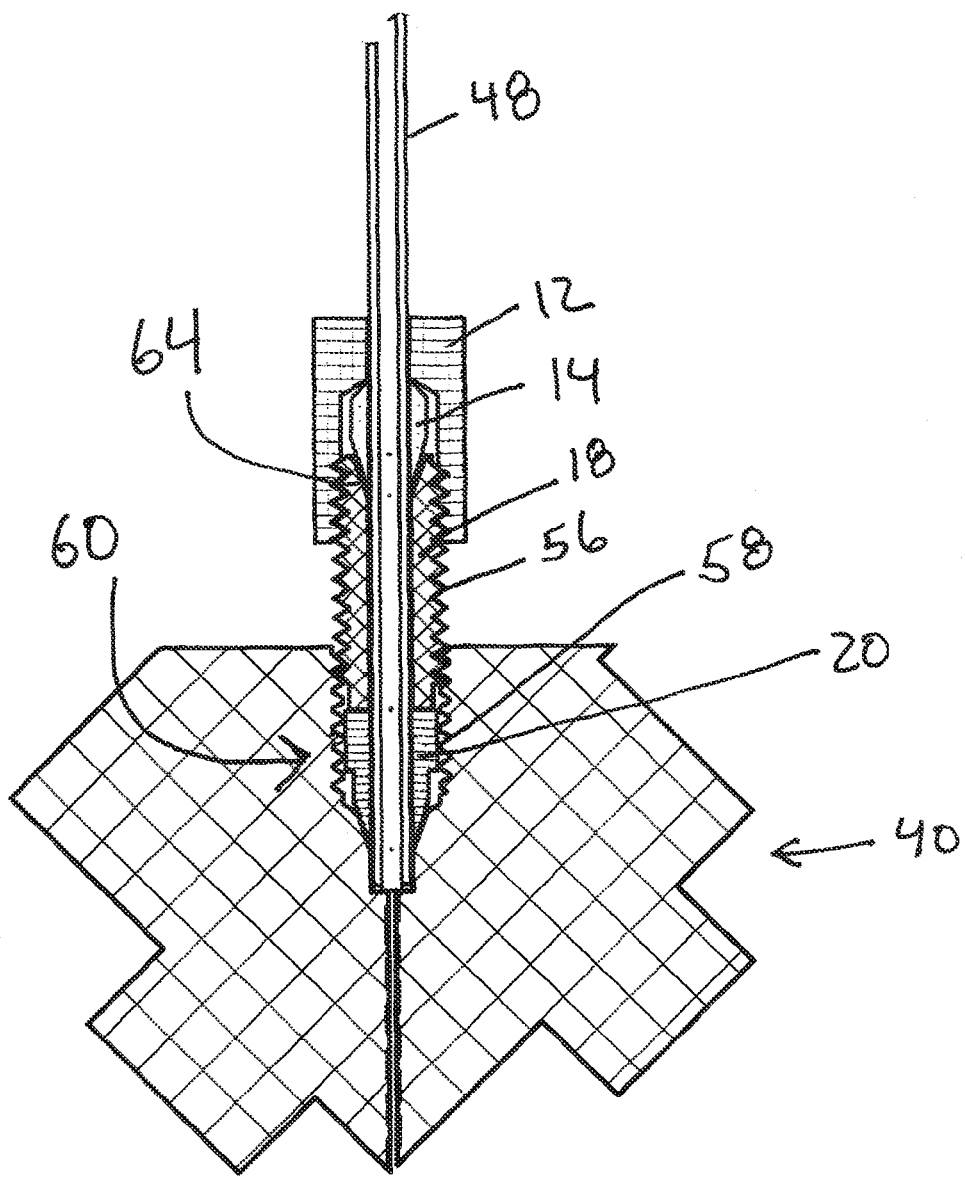
FIG. 8 is cutaway view of an exit end of tubing according to the present invention.
Figure 9:
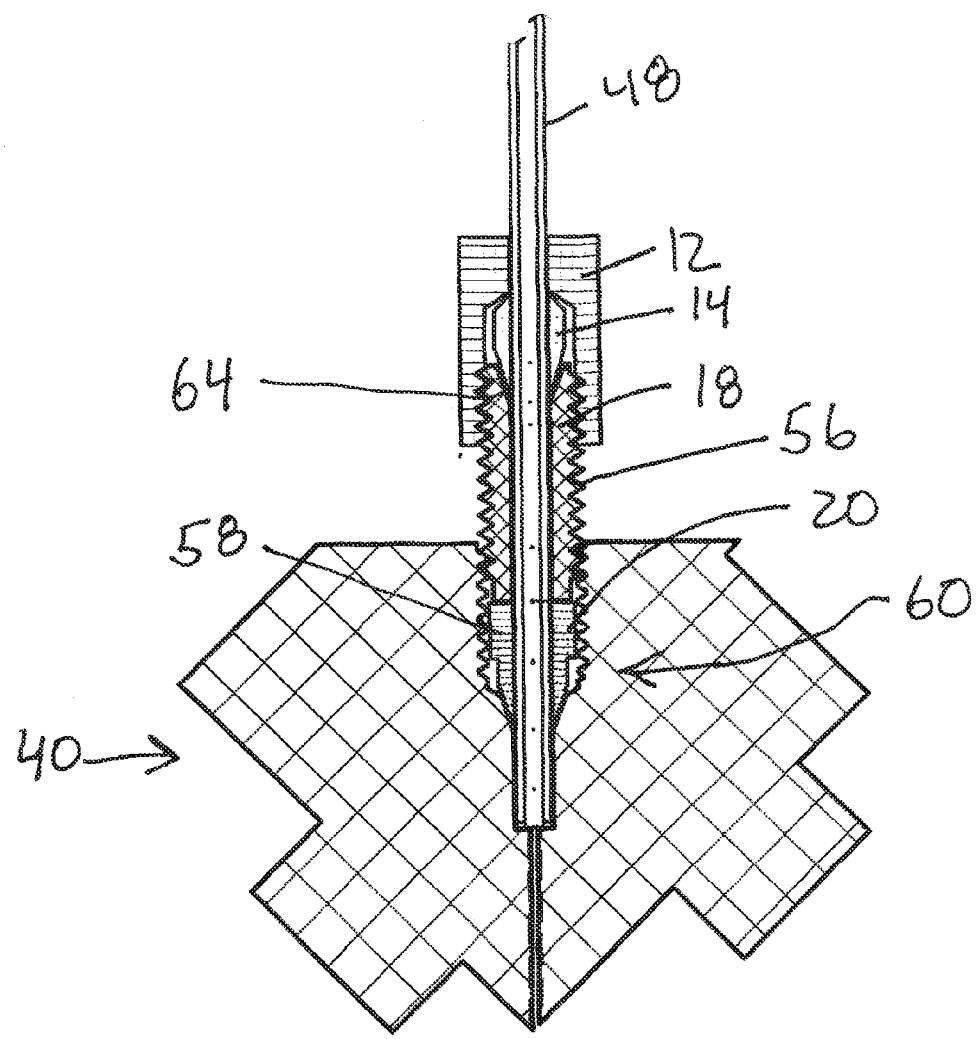
FIG. 9 is an exploded side cutaway view of a fitting according to the present invention.

The fitting body 18 includes a tubing channel 51. The fitting body 18 has an open entrance end 52 and an open exit end 54. The tubing channel 51 is open at both the entrance end 52 and the open exit end 54 of the fitting body 18 to allow passage of the tubing 48. The fitting body 18 has exterior threading 56 to allow the fitting body 18 to engage the internal threading 58 of the threaded section 60 within the CPI port 40 and allow the cap 12 to thread onto the fitting body 18, as shown in FIGS. 8-9. The fitting body 18 has a conical section 64 at the entrance end 52 of the fitting body 18 that has a geometry to receive the first ferrule 14 and allow the first ferrule 14 to be compress against tubing 48. The fitting body 18 can have an optional hex nut 66 as shown in FIG. 7 to be a stationary part of the fitting body 18 and allow the use of a wrench to aid in removal from the CPI port 40. The second ferrule 20 is a single or multi-piece cone shaped compression fitting. The second ferrule 20 includes an open entrance end 68, open exit end 70 and a through hole 72 between the entrance end 68 and exit end 70. The second ferrule 20 is constructed of compressible material which is capable of compressing radially about the tubing 48 after the tubing 48 has been inserted into the through hole 72 of the second ferrule 20.

Prior to connection of the fitting 10 to an apparatus, the fitting 10 is assembled. The tubing 48 has an outside diameter of approximately one sixteenth of an inch so as to fit snugly inside the bottom cylindrical section of the CPI port 40, which usually has a diameter slightly larger than one sixteenth of an inch. Assembly of the fitting 10 begins by passing the tubing 48 through the cap 12 and then through the first ferrule 14. The tubing 48 is then inserted through the tubing channel 51 of the fitting body 18 and the cap 12 is slightly screwed onto the threading 56 of the fitting body 18. Finally, the tubing 48 inserted through the second ferrule 20. The fitting 10 is now fully assembled and ready for use.

Figure 10:
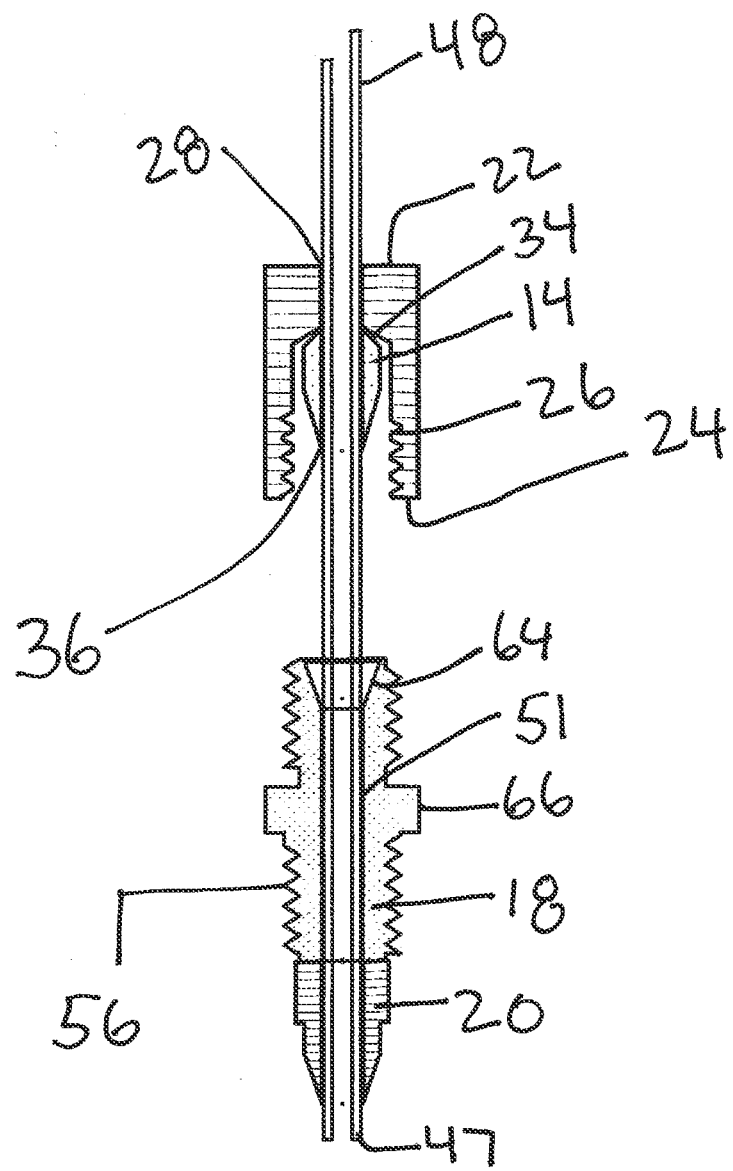
FIG. 10 is a cutaway view of a fitting according to the present invention.

The fitting 10 and tubing 48 are installed to a CPI port 40 in the following manner. Preparation of installing the fitting 10 and tubing 48 includes unscrewing the cap 12 from the fitting body 18 and pushing the tubing 48 through the first ferrule 14, fitting body 16 and second ferrule 20 so that the exit end 47 of the tubing 48 extends approximately 5 mm beyond the exit end 70 of the second ferrule 20, as shown in FIG. 10. Abnormally deep bottom cylindrical sections will require the exit end 47 of the tubing 48 to be extended farther from the exit end 70 of the second ferrule 20 as shown in the comparison of FIGS. 3 and 4. The first ferrule 14, fitting body 18 and second ferrule 20 are to be in close proximity to each other along the tubing 48. The cap 12 is replaced on the fitting body 18 without turning the cap 12 too far as to begin to compress first ferrule 14 about the tubing 48. The fitting 10 is then installed into the receiving CPI port 40 by grasping the cap 12 and guiding the exit end 47 of the tubing 48 into the CPI port 40 and pushing the fitting 10 in as far as possible, while turning the cap 12 until tight. The fitting 10 is now installed, but the mechanics of operation of the components will be reviewed for additional clarity as to the operation and attainment of the objects of the invention.

Returning to the moment when the cap 12 is first turned, it should be noted that initially the fitting body 18 begins to turn with the cap 12 and the fitting body 18 threads into the threaded section 60 of the CPI port 40. The turning action of the fitting body 18 into the threaded section 60 of the CPI port 40 pushes the second ferrule 20 into the CPI port 40. The fitting body 18 stops turning as slight pressure begins to accumulate between the second ferrule 20 and the tubing 48, due to compression of the second ferrule 20 as the second ferrule 20 enters the conical section of the CPI port 40.

During turning of the cap 12, the cap 12 begins to push against first ferrule 14 before the fitting body 18 begins to apply significant pressure against the second ferrule 20. As the cap 12 is turned, the cap 12 forces the first ferrule 14 into the conical section 64 at the entrance end 52 of the fitting body 18. The first ferrule 14 in turn grips the tubing 48 and drives the tubing 48 to the flat bottom of the CPI port 40, as the cap 12 continues to be turned. As the combination of forces resulting from first ferrule 14 tightening about the tubing 48 at the conical section 64 of the fitting body 18 begins to increase, the cap 12 begins to resist turning against the fitting body 18, causing the turning forces applied to the cap 12 to be transmitted through the first ferrule 14 and onto fitting body 18, thereby causing the fitting body 18 to again screw into the CPI port 40. As the fitting body 18 is screwed into the CPI port 40, the second ferrule 20 is driven in to the conical section of the CPI port 40, causing the second ferule 20 to be additionally compressed between the CPI port 40 and tubing 48 and providing a seal between the tubing 48 and the CPI port 40. As the second ferrule 20 begins to compress in the conical section of the CPI port 40, the second ferrule 20 offers resistance to the screwing of the fitting body 18 into the CPI port 40. As the friction between the second ferrule 20 and the tubing 48 increases due to tightening, there is greater resistance to insertion of fitting body 18 into the CPI port 40. This increased resistance causes the cap 12 to again turn relative to the fitting body 18. Even though only the cap 12 is actually being tighten by the user, there is a back and forth tightening progressing between the cap 12 tightening to the fitting body 18 and the fitting body 18 tightening in the CPI port 40. This back and forth tightening is caused by the back and forth compression of the first ferrule 14 and second ferrule 20, which ultimately results in the first ferrule 14 and second ferrule 20 achieving a proportional and approximately equal compression about the tubing 48. The total back and forth tightening and compression process happens so quickly and frequently that it is almost imperceptible. The best results will be achieved is the first ferrule 14 and the second ferrule 20 are made from a similar material and have a similar shape and size.

Once installed in the aforesaid manner, the manner of operation of the fitting 10 becomes apparent. The compression of first ferrule 14, causes friction against the tubing 48 relative to fitting body 18 that is securely attached in the CPI port 40. A fraction of longitudinal pressure which occurs at exit end 47 of the tubing 48 during normal operation of the CPI port 40 is transmitted through tubing 48 to first ferrule 14. This fraction of longitudinal pressure is then transmitted to the cap 12 and on to the threaded portion of fitting body 18, where the threads inside the cap 12 engage against fitting body 18. Then, the fraction of longitudinal pressure is transmitted through the fitting body 18 and back to the CPI port 40. The aforementioned fraction of longitudinal compressive pressure is a percentage of the total pressure in and around the exit end 47 of the tubing 48. This fraction of the total pressure force does not get retained and transmitted back to fitting body 18 of the fitting 10 through the second ferrule 20, as compared to current coupling devices. This effect amounts to the 'sharing' of forces applied to the tubing 48 between the first ferrule 14 and the second ferrule 20, giving the fitting substantially greater holding power of the tubing 48 against pressures applied at the exit end 47 of the tubing 48.

Alternately, the invention allows the primary method of sealing to be passed from the second ferrule 20 to the exit end 47 of the tubing 48. This method of sealing will be referred to as 'tip sealing', and is an entirely new method to those practiced in the state of the art. Tip sealing is accomplished by installing the fitting 10 as described above, but instead of using a sliding polymeric ferrule for the first ferrule 14, a 'biting' ferrule, or a permanently applied ferrule is employed on the tubing 48. During tip sealing, turning the cap 12 causes the first ferrule 14 of the biting ferrule type to secure the first ferrule 14 against the tubing 48, causing a greater proportion of force to be transmitted through the tubing 48 to the exit end 47 of the tubing 48, as compared to a polymeric ferrule. When tip sealing is not used, the fitting body 18 begins turning when a similar compressive equilibrium between the first ferrule 14 and the second ferrule 20 is achieved. During tip sealing, the fitting body 18 begins to turn when the cap 12 has compressed the biting ferrule into the conical section 64 of the fitting body 18. The compression of the biting ferrule transmits the rotational force of the cap 12 to the fitting body 18. This rotational force is then transmitted to the threading of the CPI port 40, which drives the exit end 47 of the tubing 48 against the flat bottom of the CPI port 40. During tip sealing, the secondary ferule 20 acts as a guide to keep the tubing 48 centered in the CPI port 40, but does not compress the second ferrule 20 about the tubing 48, so that it does not impede the exit end 47 of the tubing 48 from becoming compressed at the flat bottom of the CPI port and sealing at the flat bottom of the CPI port. This is due to the holding mechanism of the biting ferrule which is caused by shear forces between said biting ferrule and tubing 48. Most biting ferrules include an edge that digs in or bites when smaller section of the biting ferrule is compressed. This edge aides in creating the shear forces. Whereas, a 'non-biting' ferrule relies on lesser frictional forces within the ferrule's inner circumference and where these frictional forces have less holding power against slippage of tubing 48. Tip sealing is significant because it dramatically reduces the potential for chemical residuals to become entrapped in miniscule dead volumes which are associated with the perimeter of the cylindrical volume below the second ferrule 20 that interact with CPI port 40. During tip sealing, the second ferrule 20 is not required to provide sealing surfaces, rather the second ferrule 20 provides mechanical stabilization of the tubing 48 such as to hold the tubing 48 concentric with the center of the open area within the CPI port 40. Another advantage of metal-to-metal sealing between the biting ferrule and the tubing 48 that is metal is the potential of the fitting 10 to withstand pressures in excess of the limitations of the combination of current ferrules.

A malleable metal or polymer may be applied to the exit end 47 of the tubing 48, to allow a seal to be created between the exit end 47 of the tubing 48 and the flat bottom of bottom cylindrical section of the CPI port 40. The preferred material being gold, but allowing for the possibility that other materials may be employed within the spirit of the present invention.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof

I claim:

1. A method of coupling tubing to a CPI type port, comprising:
    inserting the tubing into a hole in a closed end of a cap and extending the tubing out an open end of the cap;
    inserting the tubing into an open entrance end of a first ferrule, inserting the tubing through a through hole of the first ferrule and extending the tubing out an open exit end of the first ferrule;
    inserting the tubing into an open entrance end of a fitting body, inserting the tubing through a tubing channel of the fitting body and extending the tubing out an open exit end of the fitting body;
    inserting the tubing into an open entrance end of a second ferrule, inserting a terminator pin through a through hole of the second ferrule and extending the tubing out an open exit end of the second ferrule;
    inserting the tubing into a hole in a closed end of a cap and extending the tubing out an open end of the cap;
    inserting the second ferrule, with the tubing extending out of the exit end of the second ferrule, into the CPI type port that has a threaded section, a conical section which reduces in diameter and a bottom cylindrical section, followed by inserting the fitting body having exterior threading into the CPI type port; and
    turning the cap, having interior threading at a open end of the cap, onto the exterior threading of the fitting body until the cap is tight and thereby turning the fitting body into the CPI type port as the exterior threading engages the threaded section of the CPI type port during the turning of the cap;
    forcing the first ferrule into a conical section of the entrance end of the fitting body due to turning of the cap and compressing the first ferrule about the tubing due to turning of the cap;
    forcing the second ferrule into a conical section of the CPI type port due to turning of the cap and compressing the second ferrule about the tubing due to turning of the cap; and
    wherein the moment when the cap is first turned, the fitting body begins to turn with the cap and the fitting body threads into the threaded section of the CPI type port; where the turning action of the fitting body into the threaded section of the CPI type port pushes the second ferrule into the CPI type port; wherein the fitting body stops turning as slight pressure begins to accumulate between the second ferrule and the tubing, due to compression of the second ferrule as the second ferrule enters the conical section of the CPI type port, wherein during turning of the cap, the cap begins to push against the first ferrule before the fitting body begins to apply significant pressure against the second ferrule, wherein as the cap is turned, the cap forces the first ferrule into the conical section at the first end of the fitting body and the first ferrule in turn grips the tubing and drives the tubing to the bottom of the CPI type port, as the cap continues to be turned; wherein as the combination of forces resulting from the first ferrule tightening about the tubing at the conical section of the fitting body begins to increase, the cap begins to resist turning against the fitting body, causing the turning forces applied to the cap to be transmitted through the first ferrule to the fitting body and causing the fitting body to again screw into the CPI type port, wherein as the fitting body is screwed into the CPI type port, the second ferrule is driven in to the conical section of the CPI type port, causing the second ferule to be additionally compressed between the CPI type port and tubing and providing a seal between the tubing and the CPI type port; wherein as the second ferrule begins to compress in the conical section of the CPI type port, the second ferrule offers resistance to the screwing of the fitting body into the CPI type port; wherein as the friction between the second ferrule and the tubing increases due to tightening, there is greater resistance to insertion of the fitting body into the CPI type port; wherein the increased resistance causes the cap to again turn relative to the fitting body.

2. A method of coupling a tube to a CPI type port, comprising:
    inserting tubing into a terminator pin of a malleable material;

inserting the terminator pin into a hole in a closed end of a cap and extending the terminator pin out an open end of the cap;

inserting the terminator pin into an open entrance end of a first ferrule, inserting the terminator pin through a through hole of the first ferrule and extending the terminator pin out an open exit end of the first ferrule;

inserting the terminator pin into an open entrance end of a fitting body, inserting the terminator pin through a terminator pin channel of the fitting body and extending the terminator pin out an open exit end of the fitting body;

inserting the terminator pin into an open entrance end of a second ferrule, inserting the terminator pin through a through hole of the second ferrule and extending the terminator pin out an open exit end of the second ferrule;

inserting the second ferrule, with the terminator pin extending out of the exit end of the second ferrule, into the CPI type port that has a threaded section, a conical section which reduces in diameter and a bottom cylindrical section, followed by inserting the fitting body having exterior threading into the CPI type port;

turning the cap, having interior threading at a open end of the cap, onto the exterior threading of the fitting body until the cap is tight and thereby turning the fitting body into the CPI type port as the exterior threading engages the threaded section of the CPI type port during the turning of the cap;

forcing the first ferrule into a conical section of the entrance end of the fitting body due to turning of the cap and compressing the first ferrule about the terminator pin due to turning of the cap;

forcing the second ferrule into a conical section of the CPI type port due to turning of the cap and compressing the second ferrule about the terminator pin due to turning of the cap; and wherein the moment when the cap is first turned, the fitting body begins to turn with the cap and the fitting body threads into the threaded section of the CPI type port;

where the turning action of the fitting body into the threaded section of the CPI type port pushes the second ferrule into the CPI type port; wherein the fitting body stops turning as slight pressure begins to accumulate between the second ferrule and the terminator pin, due to compression of the second ferrule as the second ferrule enters the conical section of the CPI type port, wherein during turning of the cap, the cap begins to push against the first ferrule before the fitting body begins to apply significant pressure against the second ferrule, wherein as the cap is turned, the cap forces the first ferrule into the conical section at the first end of the fitting body and the first ferrule in turn grips the terminator pin and drives the terminator pin to the bottom of the CPI type port, as the cap continues to be turned; wherein as the combination of forces resulting from the first ferrule tightening about the terminator pin at the conical section of the fitting body begins to increase, the cap begins to resist turning against the fitting body, causing the turning forces applied to the cap to be transmitted through the first ferrule to the fitting body and causing the fitting body to again screw into the CPI type port, wherein as the fitting body is screwed into the CPI type port, the second ferrule is driven in to the conical section of the CPI type port, causing the second ferule to be additionally compressed between the CPI type port and terminator pin and providing a seal between the terminator pin and the CPI type port; wherein as the second ferrule begins to compress in the conical section of the CPI type port, the second ferrule offers resistance to the screwing of the fitting body into the CPI type port; wherein as the friction between the second ferrule and the terminator pin increases due to tightening, there is greater resistance to insertion of fitting body into the CPI type port; wherein the increased resistance causes the cap to again turn relative to the fitting body.

\* \* \* \* \*